United States Patent
Foley et al.

(10) Patent No.: US 10,059,801 B2
(45) Date of Patent: Aug. 28, 2018

(54) POLYETHERS, POLYAMINES, POLYTHIOETHERS, AND METHODS FOR MAKING SAME

(71) Applicant: P2 Science, Inc., Woodbridge, CT (US)

(72) Inventors: Patrick Foley, New Haven, CT (US); Yonghua Yang, New Haven, CT (US)

(73) Assignee: P2 SCIENCE, INC., Woodbridge, CT (US)

( * ) Notice: Subject to any disclaimer, the term of this patent is extended or adjusted under 35 U.S.C. 154(b) by 0 days.

(21) Appl. No.: 15/507,640

(22) PCT Filed: Aug. 28, 2015

(86) PCT No.: PCT/US2015/047397
§ 371 (c)(1),
(2) Date: Feb. 28, 2017

(87) PCT Pub. No.: WO2016/033437
PCT Pub. Date: Mar. 3, 2016

(65) Prior Publication Data
US 2017/0283553 A1    Oct. 5, 2017

Related U.S. Application Data

(60) Provisional application No. 62/043,943, filed on Aug. 29, 2014.

(51) Int. Cl.
| | | |
|---|---|---|
| *C08G 65/34* | (2006.01) | |
| *C07C 41/01* | (2006.01) | |
| *C08G 65/00* | (2006.01) | |
| *C07C 43/178* | (2006.01) | |

(52) U.S. Cl.
CPC .............. *C08G 65/34* (2013.01); *C07C 41/01* (2013.01); *C07C 43/1785* (2013.01); *C08G 65/002* (2013.01); *C08G 2650/64* (2013.01)

(58) Field of Classification Search
CPC .. C08G 65/34; C08G 2650/64; C08G 65/002; C07C 43/1785; C07C 41/01; C07C 319/12; C07C 321/08
See application file for complete search history.

(56) References Cited

U.S. PATENT DOCUMENTS

| | | |
|---|---|---|
| 2,020,298 A | 11/1935 | Carothers et al. |
| 3,980,697 A | 9/1976 | El-Chahawi et al. |
| 4,218,379 A | 8/1980 | Harris et al. |
| 4,366,270 A | 12/1982 | Ruter |
| 4,381,416 A | 4/1983 | Kyo et al. |
| 5,264,547 A | 11/1993 | Yamaguchi et al. |
| 5,616,679 A | 4/1997 | Fies et al. |

FOREIGN PATENT DOCUMENTS

| | | |
|---|---|---|
| EP | 0841333 A1 | 5/1998 |
| GB | 1266091 | 3/1972 |
| JP | 2006 273796 A | 10/2006 |
| JP | 2008 050415 A | 3/2008 |
| WO | WO 2006/057086 | 6/2006 |

OTHER PUBLICATIONS

Nagai et al. ("The Formation of Ethers from Unsaturated Aliphatic Alcohols in the Presence of Boron Trifluoride Etherate", Bulletin of the Chemical Society of Japan, vol. 51, No. 11, Nov. 1978, pp. 3273-3276) (Year: 1978).*
Ireland et al. ("The Claisen Rearrangement of N-Allylketene O,N-Acetals", J. Org. Chem., vol. 39, No. 3, Sep. 1974, pp. 421-424). (Year: 1974).*
Desaubry et al. ("Toward higher polyprenols under 'prebiotic' conditions", Tetrahedron Letters, vol. 44, 2003, pp. 6959-6961) (Year: 2003).*
Takahashi et al. ("Cationic Polymerization Behavior of Alkoxyallenes", Macromolecules, Vo. 28, No. 4, 1995, pp. 866-869). (Year: 1995).*
Cahn et al, "Specification of Molecular Chirality", *Angew. Chem. Inter. Edit.*, 1966, vol. 5, No. 4, pp. 385-415.
Cahn and Ingold, "Specification of Configuration about Quadricovalent Asymmetric Atoms", *J. Chem. Soc.* 1951 (London), pp. 612-622.
Cahn et al., "The Specification of Asymmetric Configuration in Organic Chemistry", *Experientia*, 1956, vol. 12, pp. 81-94.
Cahn, "An Introduction to the Sequence Rule. A system for the specification of absolute configuration", *Journal of Chemical Education*, 1964 (London), vol. 41, No. 3, pp. 116-125.
Nagai, "The Formation of Ethers from dl-Citronellol in the Presence of Boron Trifluoride Etherate", *Bull. Chem. Soc. Jap.*, 1976, vol. 49, pp. 265-269.
Abstract of Japanese Patent Application No. 2006-273796 published Oct. 12, 2006 (1 page).
Abstract of Japanese Patent Application No. 2008-050415 published Mar. 6, 2008 (1 page).

* cited by examiner

*Primary Examiner* — Rosalynd A Keys
(74) *Attorney, Agent, or Firm* — Hoxie & Associates LLC

(57) ABSTRACT

The invention relates to polyethers, polyamines, and polythioethers, as well as to processes for synthesizing them, e.g., using olefins as starting material.

23 Claims, 1 Drawing Sheet

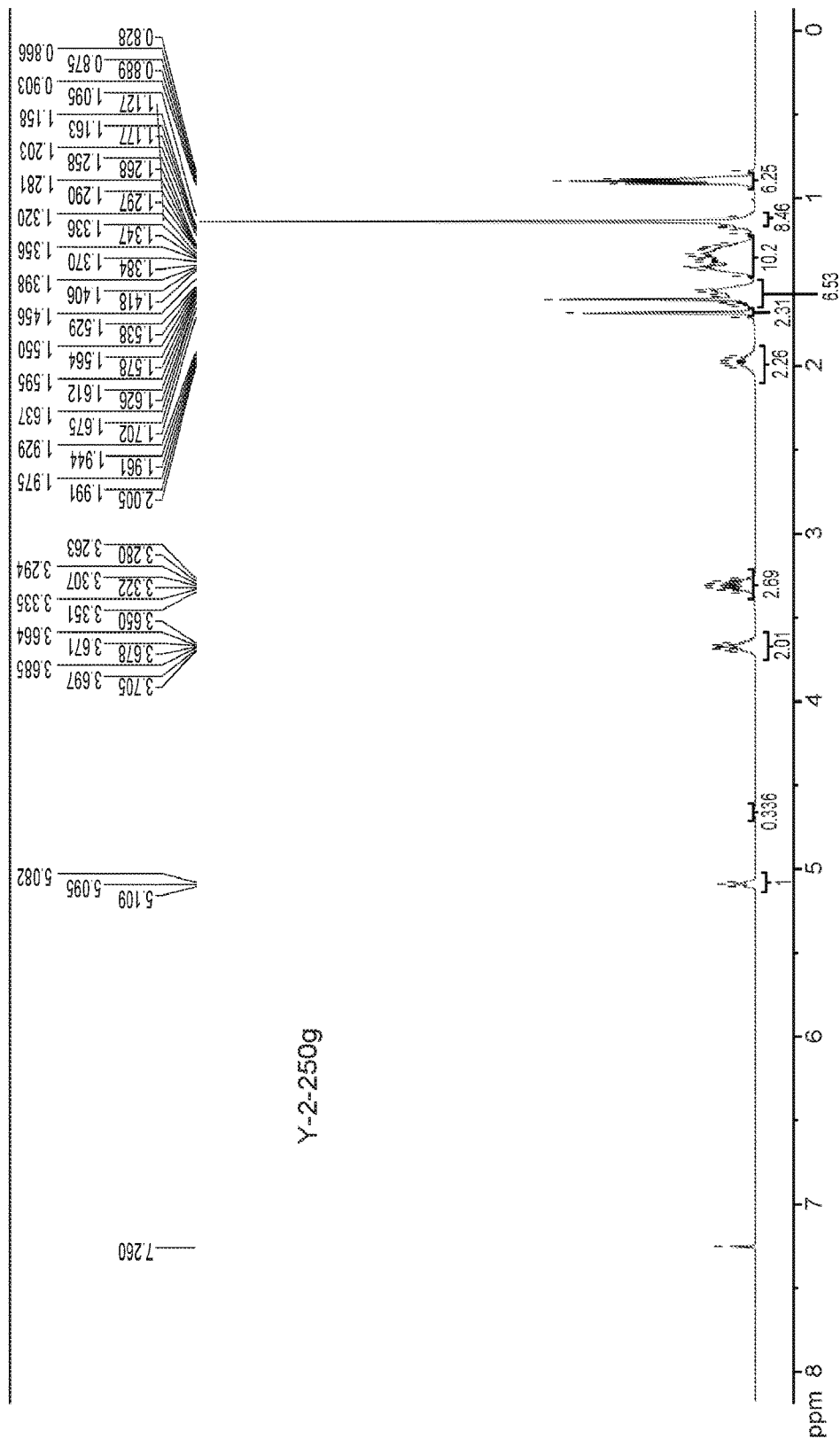

POLYETHERS, POLYAMINES, POLYTHIOETHERS, AND METHODS FOR MAKING SAME

RELATED APPLICATIONS

This application is a U.S. National Phase application, filed under 35 U.S.C. § 371(c), of International Application No. PCT/US2015/047397, filed Aug. 28, 2015, which claims the benefit of and priority to U.S. Provisional Patent Application No. 62/043,943, filed Aug. 29, 2014, titled, "POLYETHERS, POLYAMINES, POLYTHIOETHERS, AND METHODS FOR MAKING SAME", the entireties of each of which are incorporated by reference herein for all purposes.

BACKGROUND OF THE INVENTION

Polymer compounds, and specifically polyethers, polyamines, and polythioethers have found use as lubricants, emollients, humectants, and surfactants. Compounds of the invention may be used in cosmetic or specialty chemical formulations and in some instances may be used as naturally derived alternatives to silicone polymers.

New polymerization approaches that allow for the use of different starting materials and the incorporation of new functional groups are desired. Polymers are formulated into various specialty chemical applications, including personal care, to alter and improve the function of the product. The functionality of the polymer depends on its size and composition, and new and renewable compositions are highly desired as they have the potential to improve application performance.

SUMMARY OF THE INVENTION

In one aspect, the invention features a compound according to Formula I:

Formula I or a salt thereof, wherein,
$R^1$ is a bond, optionally substituted $C_1$-$C_{12}$ alkyl, optionally substituted $C_2$-$C_{12}$ alkenyl, or optionally substituted $C_2$-$C_{12}$ alkynyl; for example, the alkyl or alkenyl group may be a branched alkyl or alkenyl group, e.g., the optional substitution is alkyl, e.g., a methyl group.
X is O, NH, or S;
one of the ===== is a double bond and the other ===== is a single bond; and
n is an integer between 1 and 10,000.

In another aspect, the invention features a method of producing a compound of Formula I or a salt thereof. The method includes reacting a compound of Formula II or Formula III:

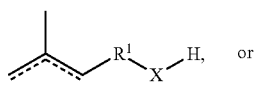

Formula II or

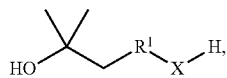

Formula III with a Lewis or Bronsted acid (e.g., methanesulfonic acid) to obtain a compound of Formula I or a salt thereof:

Formula I wherein,
$R^1$ is a bond, optionally substituted $C_1$-$C_{12}$ alkyl, optionally substituted $C_2$-$C_{12}$ alkenyl, or optionally substituted $C_2$-$C_{12}$ alkynyl;
X is O, NH, or S;
one of the ===== is a double bond and the other ===== is a single bond; and
n is an integer between 1 and 10,000, Suitable Lewis acid catalysts include tin, zinc, aluminum, and boron based molecules, as well as many lanthanide and actinide-type lewis acids. Suitable Bronsted acids include sulfuric acid, hydrochloric acid, methanesulfonic acid, tosic acid, phosphoric acid, trifluoroacetic acid, and trichloroacetic acid.

Unless otherwise defined, all technical and scientific terms used herein have the same meaning as commonly understood by one of ordinary skill in the art to which this invention belongs. In the specification, the singular forms also include the plural unless the context dearly dictates otherwise. Although methods and materials similar or equivalent to those described herein can be used in the practice or testing of the present invention, suitable methods and materials are described below. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 1 is a $^1$H NMR spectrum of polycitronellol.

DETAILED DESCRIPTION OF THE INVENTION

New polymerization approaches that allow for the use of different starting materials and the incorporation of new functional groups are disclosed herein. Polymers generated by the methods described herein may be formulated into various specialty chemical applications, including personal care, to alter and improve the function of such products. The functionality of the polymer depends on its size and composition, and new and renewable compositions are highly desired as they have the potential to improve application performance.

In one aspect, the invention features a compound according to Formula I:

Formula I or a salt thereof, wherein,
$R^1$ is a bond, optionally substituted $C_1$-$C_{12}$ alkyl, optionally substituted $C_2$-$C_{12}$ alkenyl, or optionally substituted $C_2$-$C_{12}$ alkynyl;
X is O, NH, or S;
one of the ===== is a double bond and the other ===== is a single bond; and
n is an integer between 1 and 10,000.

In some embodiments, X is O.

In some embodiments, X is NH.

In some embodiments, X is S.

In some embodiments, $R^1$ is optionally substituted linear $C_1$-$C_{12}$ alkyl or branched $C_3$-$C_{12}$ alkyl.

In some embodiments, $R^1$ is unsubstituted linear $C_1$-$C_{12}$ alkyl or branched $C_3$-$C_{12}$ alkyl.

In some embodiments, $R^1$ is unsubstituted linear $C_1$-$C_{12}$ alkyl.

In some embodiments, $R^1$ is unsubstituted branched $C_3$-$C_{12}$ alkyl.

In some embodiments, $R^1$ is optionally substituted linear $C_2$-$C_{12}$ alkenyl or branched $C_3$-$C_{12}$ alkenyl.

In some embodiments, $R^1$ is unsubstituted linear $C_2$-$C_{12}$ alkenyl or branched $C_3$-$C_{12}$ alkenyl.

In some embodiments, $R^1$ is unsubstituted linear $C_2$-$C_{12}$ alkenyl.

In some embodiments, $R^1$ is unsubstituted branched $C_3$-$C_{12}$ alkenyl.

In some embodiments, n is greater than 1 (e.g., between 2 and about 100, between about 100 and about 1,000, between about 1,000 and about 5,000, between about 5,000 and about 10,000).

In some embodiments, n is 1, 2, 3, 4, 5, 6, 7, 8, 9, or 10.

In some embodiments, n is 2 or 3.

In another aspect, the invention features a method of producing a compound of Formula I or a salt thereof. The method includes reacting a compound of Formula II or Formula III:

Formula II

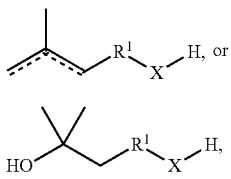

Formula III with methanesulfonic acid to obtain a compound of Formula I or a salt thereof:

Formula I

wherein,
$R^1$ is a bond, optionally substituted $C_1$-$C_{12}$ alkyl, optionally substituted $C_2$-$C_{12}$ alkenyl, or optionally substituted $C_2$-$C_{12}$ alkynyl;
X is O, NH, or S;
one of the ===== is a double bond and the other ===== is a single bond; and
n is an integer between 1 and 10,000.

In some embodiments, the reaction of a compound of Formula II or Formula III with methane sulfonic acid comprises an incubation step, quenching step, a phase separation step, and a distillation step.

In some embodiments, the incubation step occurs at room temperature.

In some embodiments, the incubation step occurs over four days.

In some embodiments, the distillation step occurs at 85° C.

In some embodiments, the distillation step occurs at 1.5 mbar.

In some embodiments, a compound of Formula II (e.g., citronellol) is combined with methanesulfonic acid and stirred (e.g., at room temperature) (e.g., for four days). The reaction progress is monitored (e.g., by $^1$H NMR). The reaction is then quenched (e.g., by adding 1 M NaOH). A polar solvent (e.g., ethyl acetate) is added and the phases are separated. The organic phase is then washed (e.g., with brine). The polar solvent is then removed (e.g., by evaporation). Subsequently, vacuum distillation is applied (e.g., using a short-path wiped-film distillation system) (e.g., at 85° C.) (e.g., at 1.5 mbar) to remove unreacted starting material and low boiling point chemicals. Finally, the average molecular weight and yield of the polymer product is determined. Methods for the formation of ethers from Citronellol using boron trifluoride etherate were described by Nagai. Nagai, Bill, Chem. Soc. Jap. 49(1), 265-269 (1976).

In some embodiments, an amidation step occurs, wherein a compound of Formula I, wherein X is O, reacts with NH3 under an elevated pressure to obtain a corresponding compound of Formula I, wherein X is NH.

The process described herein can be applied using many different combinations of olefinic alcohols, resulting in a large variety of new compositions of matter. Further, the olefinic alcohols can be hydroxylated or alkoxylated at the most highly substituted carbon of the olefin and used as a functional equivalent to the olefin. For example, Scheme 2 shows functional equivalents for this process, where $R^1$ is as defined in Formula I above.

Scheme 2

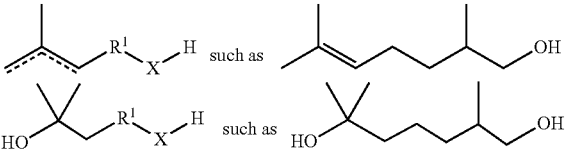

Non-limiting examples of suitable olefinic alcohols for the processes described herein include those depicted in Table 1 below, as well as their substituted and/or unsaturated analogs and functional equivalents. One of the ===== is a double bond and the other ===== is a single bond.

TABLE 1

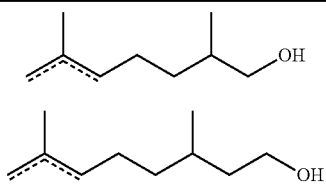

TABLE 1-continued

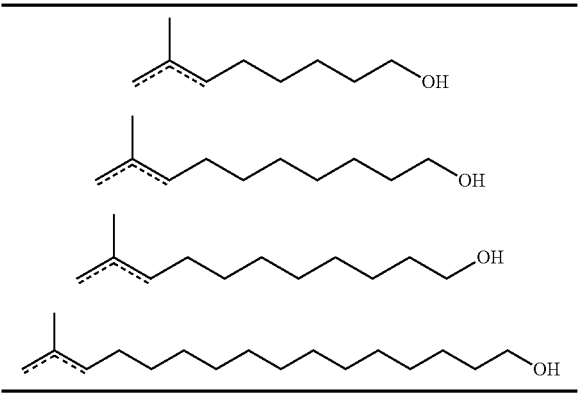

Several of the molecules in Table 1, above, can be derived from renewable resources such as terpenes (e.g., citronellic acid and/or citronellenes) or unsaturated vegetable oil fatty acids or alcohols. When obtaining these molecules from unsaturated fatty acids or alcohols, metathesis of the fatty acids or alcohols with a suitable olefin such as isobutylene or 2,3-dimethylbutene, or reductive ozonolysis followed by Wittig-type olefination, may yield suitable starting materials. Metathesis of fatty acids or alcohols may also give rise to internal olefins that can then undergo olefin isomerization to produce compounds of the type described in Table 1. In general, the olefins and corresponding functional equivalents can also be made by adding organometallic species to esters, performing Wittig- or Horner-Wadsworth-Emmons-type olefinations of aldehydes, or by performing metathesis reactions on suitable olefin precursors.

The polymers obtained from this process may possess alcohol and olefinic terminal groups, as indicated in Formula I. These alcohol and olefinic groups can be used to further grow the polymer and add additional functionality. Methods to prepare and grow olefinic polymers include free radical polymerization, metathesis polymerization, anionic polymerization, and/or cationic polymerization. Table 2 below includes representative polymers that can be obtained by the processes described herein, where n is as defined in Formula I above.

TABLE 2

| COMPOUND NUMBER | STRUCTURE |
|---|---|
| 101 | 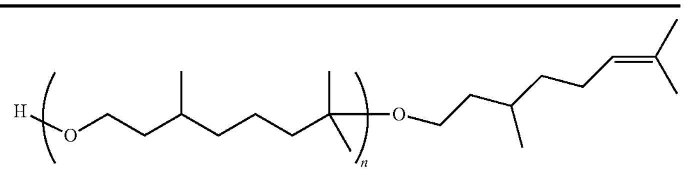 |

Definitions

The details of one or more embodiments of the invention are set forth in the accompanying description below. Unless defined otherwise, all technical and scientific terms used herein have the same meaning as commonly understood by one of ordinary skill in the art to which this invention belongs. In the case of conflict, the present specification will control.

Unless otherwise indicated, it is to be understood that the terminology used herein is for the purpose of describing particular embodiments only and is not intended to be limiting. In this specification and in the claims that follow, reference will be made to a number of terms, which shall be defined to have the definitions set forth below.

As used herein, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

As used herein, the phrase "having the formula" or "having the structure" is not intended to be limiting and is used in the same way that the term "comprising" is commonly used.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951

(London), 612; Cahn et al., *Experientia* 1956, 12, 81; Cahn, *J. Chem. Educ.* 1964, 41, 116). In some formulae of the present application, one or more chiral centers are identified by an asterisk placed next to the chiral carbon. In other formulae, no chiral center is identified, but the chiral isomers are nonetheless covered by these formulae.

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Some compounds of the present invention can exist in a tautomeric form which is also intended to be encompassed within the scope of the present invention. "Tautomers" refers to compounds whose structures differ markedly in arrangement of atoms, but which exist in easy and rapid equilibrium. It is to be understood that the compounds of the invention may be depicted as different tautomers. It should also be understood that when compounds have tautomeric forms, all tautomeric forms are intended to be within the scope of the invention, and the naming of the compounds does not exclude any tautomeric form. Further, even though one tautomer may be described, the present invention includes all tautomers of the present compounds.

As used herein, the term "salt" can include acid addition salts including hydrochlorides, hydrobromides, phosphates, sulfates, hydrogen sulfates, alkylsulfonates, arylsulfonates, acetates, benzoates, citrates, maleates, fumarates, succinates, lactates, and tartrates; alkali metal cations such as $Na^+$, $K^+$, $Li^+$, alkali earth metal salts such as $Mg^{2+}$ or $Ca^{2+}$, or organic amine salts, or organic phosphonium salts.

The term "alkyl" as used herein refers to a monovalent or bivalent, branched or unbranched saturated hydrocarbon group typically although not necessarily containing 1 to about 12 carbon atoms, such as methyl, ethyl, n-propyl, isopropyl, n-butyl, isobutyl, t-butyl, octyl, and the like.

The term "alkenyl" as used herein refers to a monovalent or bivalent, branched or unbranched, unsaturated hydrocarbon group typically although not necessarily containing 2 to about 12 carbon atoms and 1-10 carbon-carbon double bonds, such as ethylene, n-propylene, isopropylene, n-butylene, isobutylene, t-butylene, octylene, and the like.

The term "alkynyl" as used herein refers to a monovalent or bivalent, branched or unbranched, unsaturated hydrocarbon group typically although not necessarily containing 2 to about 12 carbon atoms and 1-6 carbon-carbon triple bonds, such as ethyne, propyne, butyne, pentyne, hexyne, heptyne, octyne, and the like.

By "substituted" as in "substituted alkyl," "substituted alkenyl," "substituted alkynyl," and the like, it is meant that in the alkyl, alkenyl, alkynyl, or other moiety, at least one hydrogen atom bound to a carbon atom is replaced with one or more non-hydrogen substituents, e.g., by a functional group.

Examples of functional groups include, without limitation: halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), -phosphino (—PH$_2$), mono- and di-($C_1$-$C_{24}$ alkyl)-substituted phosphino, mono- and di-($C_5$-$C_{20}$ aryl)-substituted phosphino; and the hydrocarbyl moieties such as $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above. For example, the alkyl or alkenyl group may be branched. For example, the "substituent" is an alkyl group, e.g., a methyl group.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention.

All percentages used herein, unless otherwise indicated, are by volume.

All ratios used herein, unless otherwise indicated, are by molarity.

EXAMPLES

Example 1

Synthesis of Polycitronellol

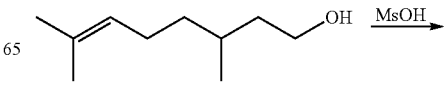

-continued

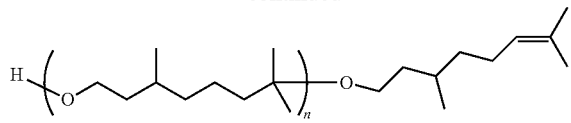

Where n = 1-20 and average n > 2

Citronellol (414 g, 2.65 mol) was treated neat with methanesuflonic acid (41.4 g) and allowed to stir at room temperature for four days. The reaction was monitored by $^1$H NMR during the process. The reaction was quenched by adding 1 M NaOH solution (430 mL). Ethyl acetate (300 mL) was added to facilitate phase separation. The organic phase was then washed with brine (200 mL). After the ethyl acetate was removed by evaporation under reduced pressure, vacuum distillation was applied using a short-path, wiped film distillation system to remove all the unreacted citronellol and low boiling point chemicals (85° C., 1.5 mbar). A total of 144 g of polymer was obtained with average molecular weight >313 Da.

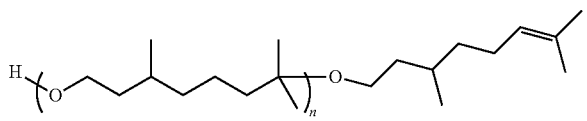

polycitronellol $^1$H NMR (CDCl$_3$, 500 MHz) δ 0.87-0.90 (m, 6.25 H, —CH$_3$), 1.10-1.18 (m, 8.46H, —CH$_3$, —CH$_2$—), 1.26-1.46 (m, 10.2H, —CH$_2$—), 1.53-1.64 (m, 6.53H, —CH$_2$—, —CH$_3$), 1.70 (s, 2.31H, —CH$_3$), 1.93-2.01 (m, 2.26H, —CH—), 2.26-3.35 (m, 2.69H, —CH$_2$O), 3.65-3.71 (m, 2.01H, —CH$_2$O), 4.65 (s, 0.16H. =CH$_2$), 4.68 (s, 0.11H, =CH$_2$), 5.10 (t, J=6.5Hz, 1H, =CH).

INCORPORATION BY REFERENCE

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed:

1. A compound according to Formula I:

Formula I or a salt thereof, wherein,
R1 is a bond, optionally substituted C2-C12 alkyl, optionally substituted C2-C12 alkenyl, or optionally substituted C2-C12 alkynyl;
X is O, NH, or S;
one of the ===== is a double bond and the other ===== is a single bond; and
n is an integer between 2 and 100, provided that the compound of Formula I is not a compound wherein R1 is a bond, X is O and n is 2.

2. The compound of claim 1, wherein X is O.
3. The compound of claim 1, wherein X is NH.
4. The compound of claim 1, wherein X is S.
5. The compound of claim 1, wherein R1 is optionally substituted branched C3-C12 alkyl.
6. The compound of claim 1, wherein R1 is unsubstituted branched C3-C12 alkyl.
7. The compound of claim 1, wherein R1 is optionally substituted linear C2-C12 alkenyl or branched C3-C12 alkenyl.
8. The compound of claim 1, wherein R1 is unsubstituted linear C2-C12 alkenyl or branched C3-C12 alkenyl.
9. The compound of claim 1, wherein n is 2, 3, 4, 5, 6, 7, 8, 9, or 10.
10. The compound of claim 1, wherein n is 2 or 3.
11. A method of producing a compound of claim 1, or a salt thereof, comprising reacting a compound of Formula II or Formula III:

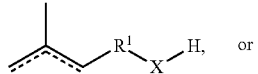

Formula II

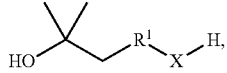

Formula III with methanesulfonic acid to obtain a compound of Formula I or a salt thereof:

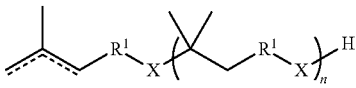

Formula I wherein,
R1 is a bond, optionally substituted C2-C12 alkyl, optionally substituted C2-C12 alkenyl, or optionally substituted C2-C12 alkynyl;
X is O, NH, or S;
one of the ===== is a double bond and the other ===== is a single bond; and
n is an integer between 2and 100.

12. The method of claim 11, wherein the reaction of a compound of Formula II or Formula III with methane sulfonic acid comprises an incubation step, quenching step, a phase separation step, and a distillation step.
13. The method of claim 12, wherein the incubation step occurs at room temperature.
14. The method of claim 12, wherein the incubation step occurs over four days.
15. The method of claim 11, wherein the distillation step occurs at 85° C.
16. The method of claim 11, wherein the distillation step occurs at 1.5 mbar.
17. The method of claim 11, further comprising an amidation step, wherein a compound of Formula I, wherein X is O, reacts with NH3 under an elevated pressure to obtain a corresponding compound of Formula I, wherein X is NH.

18. The method of claim 11, wherein the compound of Formula II is selected from the group consisting of:

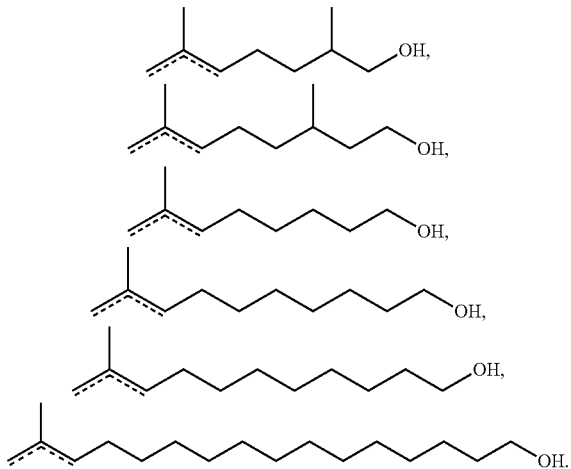

19. The method of claim 11, wherein the compound of Formula II is citronellol.

20. The compound according to claim 1, wherein the compound of Formula I is:

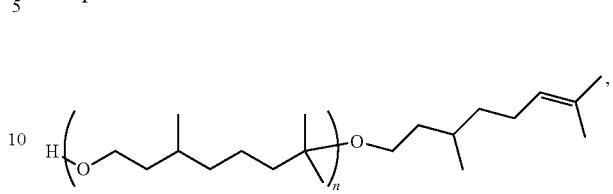

wherein n is an integer between 2 and 100, or a salt thereof.

21. The compound according to claim 20, wherein n is 2, 3, 4, 5, 6, 7, 8, 9, or 10.

22. A cosmetic or personal care composition comprising the compound according to claim 1.

23. A cosmetic or personal care composition comprising the compound according to claim 20.

* * * * *